(12) United States Patent
Owen

(10) Patent No.: US 6,562,050 B1
(45) Date of Patent: May 13, 2003

(54) EQUIPMENT FOR MICRODERMABRASION

(75) Inventor: Donald R. Owen, Kenner, LA (US)

(73) Assignee: Vital Assist, Inc., Harahan, LA (US)

( * ) Notice: Subject to any disclaimer, the term of this patent is extended or adjusted under 35 U.S.C. 154(b) by 220 days.

(21) Appl. No.: 09/653,270

(22) Filed: Sep. 1, 2000

Related U.S. Application Data (60) Provisional application No. 60/167,949, filed on Nov. 29, 1999.

(51) Int. Cl.[7] .............................................. A61B 17/50
(52) U.S. Cl. ..................................................... 606/131
(58) Field of Search ............................ 606/1, 131, 132, 606/167

(56) References Cited

U.S. PATENT DOCUMENTS

| | | | |
|---|---|---|---|
| 5,037,431 A | 8/1991 | Summers et al. | 606/131 |
| 5,037,432 A | 8/1991 | Molinari | 606/131 |
| 5,100,412 A | 3/1992 | Rosso | 606/131 |
| 5,810,842 A | 9/1998 | Di Fiore et al. | 606/131 |

FOREIGN PATENT DOCUMENTS

IT    1184922    6/1994

*Primary Examiner*—David O. Reip
(74) *Attorney, Agent, or Firm*—Jones, Walker, Waechter, Poitevent, Carrere & Denegre, L.L.P.

(57) ABSTRACT

The invention includes an improved handpiece for use in a microdermabrasion system. The handpiece includes a control line which allows the user to easily control activation of the compressor, a vacuum line and a compressor line. The microdermabrasion system includes a vacuum pump, compressor, and a mixing bottle. A pressure sensor is used to detect pressure changes in the system for use in activating/deactivating the compressor.

18 Claims, 10 Drawing Sheets

S1 normally open below 4-6"Hg, closed above this value
S2 normally open below 7-8"Hg, closed above this value
S3 normally open below 14-16"Hg, closed above this value

EQUIPMENT FOR MICRODERMABRASION

BACKGROUND OF THE INVENTION

This application claims priority of U.S. Provisional Application Ser. No. 60/167,949 filed on Nov. 29, 1999. This invention relates to a device for microdermabrasion. More particularly, this invention relates to a handpiece for microdermabrasion, which allows the user to control activation of a compressor. The device also includes an improved control mechanism for activation of the compressor.

FIELD OF THE INVENTION

PRIOR ART

Microdermabrasion ("MDA") is a term to describe the use of an air stream with entrained small particles such as aluminum oxide or hydroxide to impinge on to the stratum corneum or top layer of skin.

The devices used to deliver the stream of particles are varied. Positive pressure or grit blasting devices are composed of a compressor, grit or abrasive reservoir through which the air stream from the compressor passes in a confined space, to a nozzle placed near the skin. There is an obvious problem with abrasive and tissue debris not being easily confined by this technique. In compressor assisted systems, a compressor is connected to the mixing bottle and when the compressor is activated, air is pushed through the mixing bottle, and outputs a stream of air with entrained particles to the handpiece. One such prior art device is shown in U.S. Pat. No. 5,810,842, hereby incorporated by reference. In this device, the compressor is activated by a footswitch. The use of a footswitch is considered a drawback, as the operator requires good eye/foot coordination to effectively control the compressor and the resulting stream of particles through the handpiece.

Negative pressure or vacuum pump only based systems have the abrasive material pulled through the circuit with the skin acting as a control valve. In vacuum driven systems, a handpiece, which is open on one end, has one line in fluid communication with a source of particles. The particles are usually contained in a mixing bottle. The handpiece has a second line in fluid communication with a source of vacuum. When the open end of the handpiece is placed against the skin (the skin contact area), the opening is closed and the vacuum will draw particle from the mixing bottle into the handpiece, where they will contact the skin. The resulting used particles and abraded skin is then removed through the vacuum line. The handpiece is then moved across the area to be treated. Unfortunately, vacuum only systems, to be effective, must employ relatively high vacuum. High vacuums required for high abrasive flows require significant distortion of the skin, which can lead to bruising. This is especially relevant if larger hand piece orifices (i.e., greater distortion of the skin) are used. The greater the vacuum the more crystal impinges on the skin surface. However, also the more disruption to the underlying dermis. This can actually bruise or result in broken capillaries in sun-damaged or mature skin.

When the two systems are combined the vacuum pump is "pulling" the air/crystal through the handpiece while the compressor is "pushing" air/crystal through the handpiece. The combined systems provide flexibility by allowing the vacuum levels to be maintained at low levels while allowing the user to adjust the levels of particle velocity by changing the air flow from the compressor. However, in combined systems the activation of the compressor becomes an issue.

SUMMARY OF THE INVENTION

The present invention includes a handpiece that has a control line, which allows the user to control the pressure levels present in the working area of the handpiece. The operator's hands easily operate the control line. In conjunction with the handpiece, the invention includes a pressure sensor for detecting changes in pressure in the working area of the handpiece. The pressure sensor is used in conjunction with switches to activate or deactivate a compressor.

It is an object of the invention to provide a microdermabrasion system where the compressor is activated with the operator's hand.

It is an object of the invention to provide a pressure sensitive switch for operating a compressor in a MDA system.

It is an object of the invention to provide a MDA system which automatically stops the flow of particles when the working surface is removed form the skin.

It is an object of the invention to provide an MDA handpiece, which can have a large working footprint but still be conformable to hold.

DETAILED DESCRIPTION

The System in General

Figure 1:
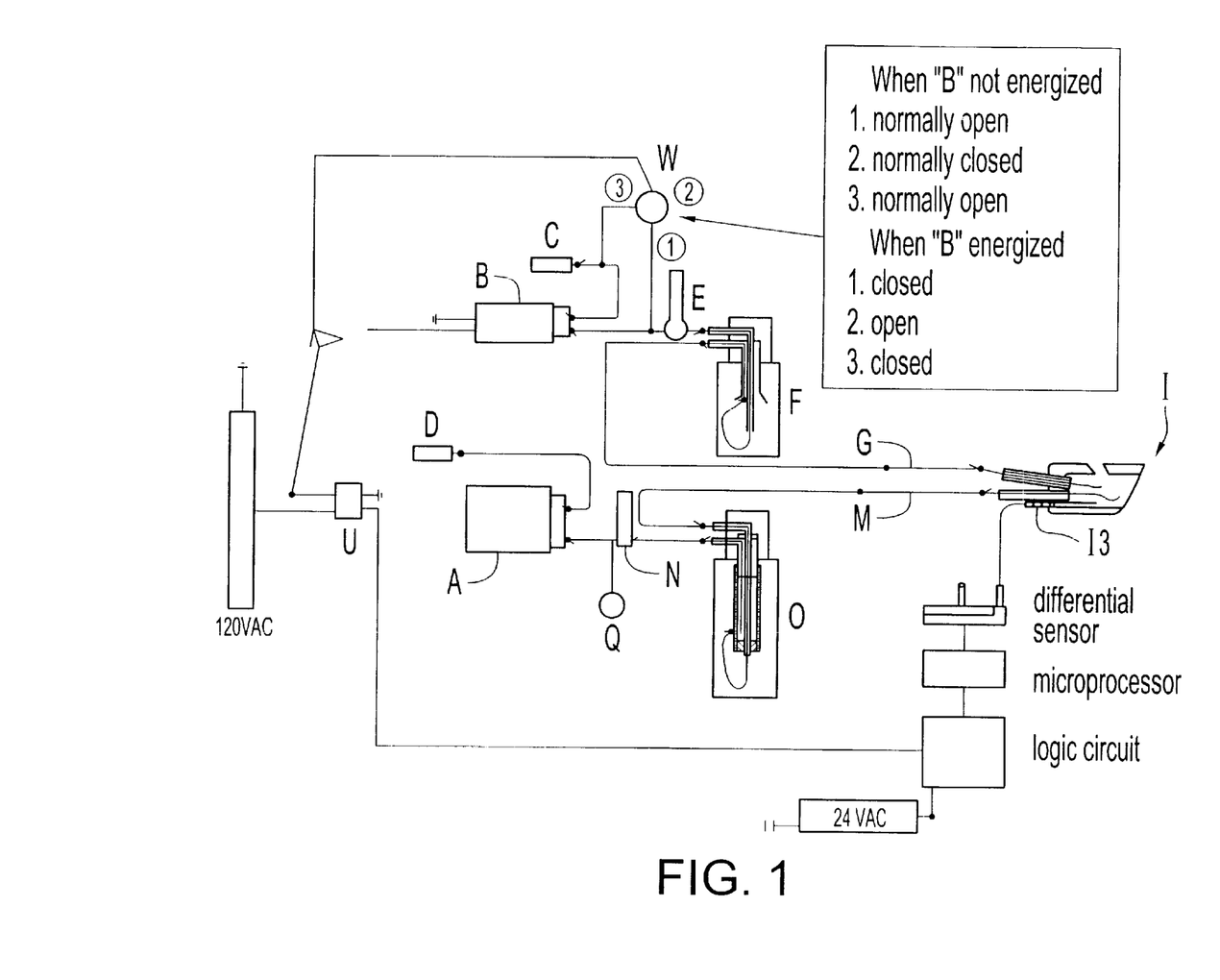
FIG. 1 shows a schematic of a basic MDA system.
Figure 5:
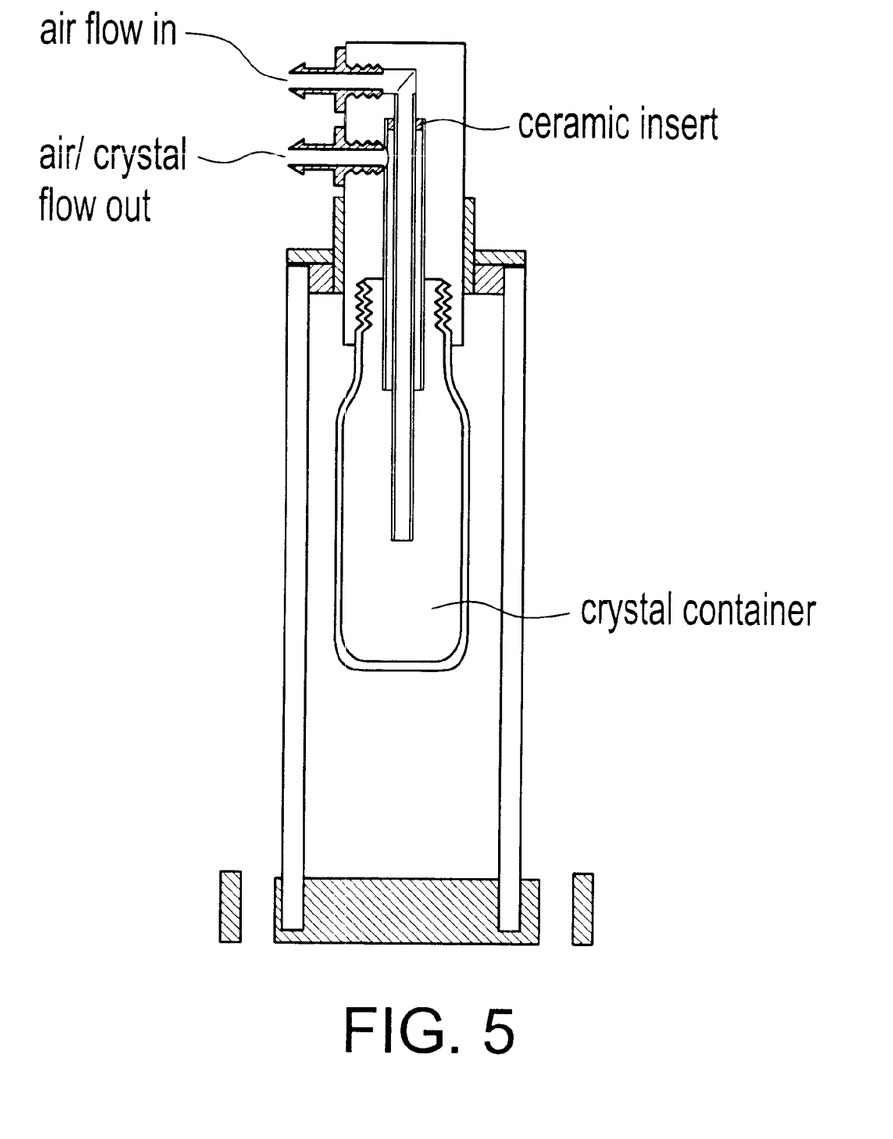
FIG. 5 shows cross sections of one embodiment of the mixing bottle.
Figure 6:
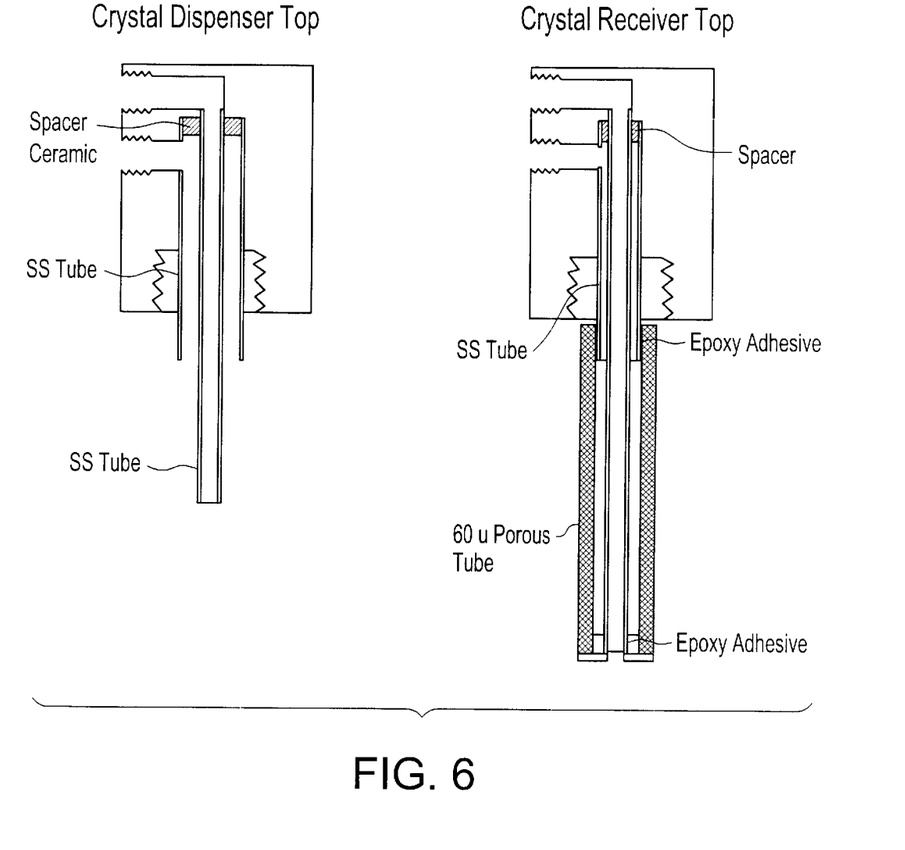
FIG. 6 shows a cross section of the crystal dispenser in the mixing bottle.

The general components of a pressure assisted MDA system are shown in FIG. 1. In the most general sense, an MDA system, as used in herein, includes the following minimum features: a handpiece I, a source of air (compressor B) and a vacuum generating device (vacuum pump A). As shown in FIG. 1, the handpiece I is fluidly connected to the vacuum pump A through line M, and fluidly connected to a compressor B through line G. Disposed between the handpiece I and vacuum pump A is a collection bottle O, and a filter may be placed between the collection bottle O and the vacuum pump A. Disposed between the handpiece I and the compressor B is a mixing bottle F, and a filter may be placed between the mixing bottle F and the compressor B. The mixing bottle F (detailed in FIGS. 5 and 6) contains the particles or abrasives, while the collection bottle O is used to contain spent particles and abraded skin. Other components are also present (such as meters, gauges, relays, switches, and valves).

In operation, the system is powered up, providing power to the vacuum pump A. The handpiece I is place against the skin to be treated, and the compressor B is activated as later described. The action of the vacuum pump A and compressor B forces air through the mixing bottle F where abrasive particles are picked up and moved through line G to the handpiece I. The air stream and entrained particles is directed against the skin through the handpiece I. The abraded skin particles and spent particles are then transmitted through line M to the collection bottle O where they are stored for disposal. Filters may be present to protect the compressor and vacuum pump from contamination with particles.

Prior systems controlled the operation of the compressor with foot switches. The present invention uses a novel handpiece in connection with a pressure switch means to operate the compressor.

Figure 2:
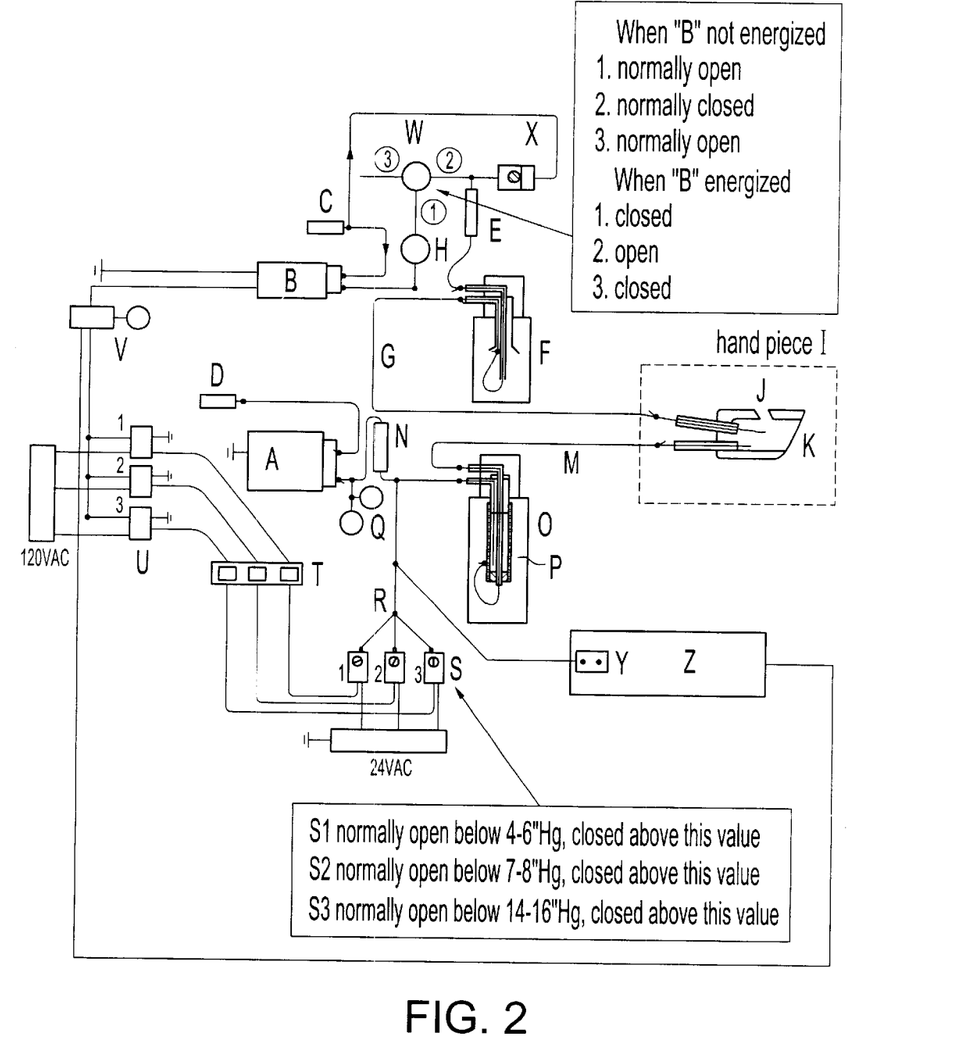
FIG. 2 shows a schematic of one embodiment of an MDA system using both pneumatics switch control and microprocessor control.
Figure 3:
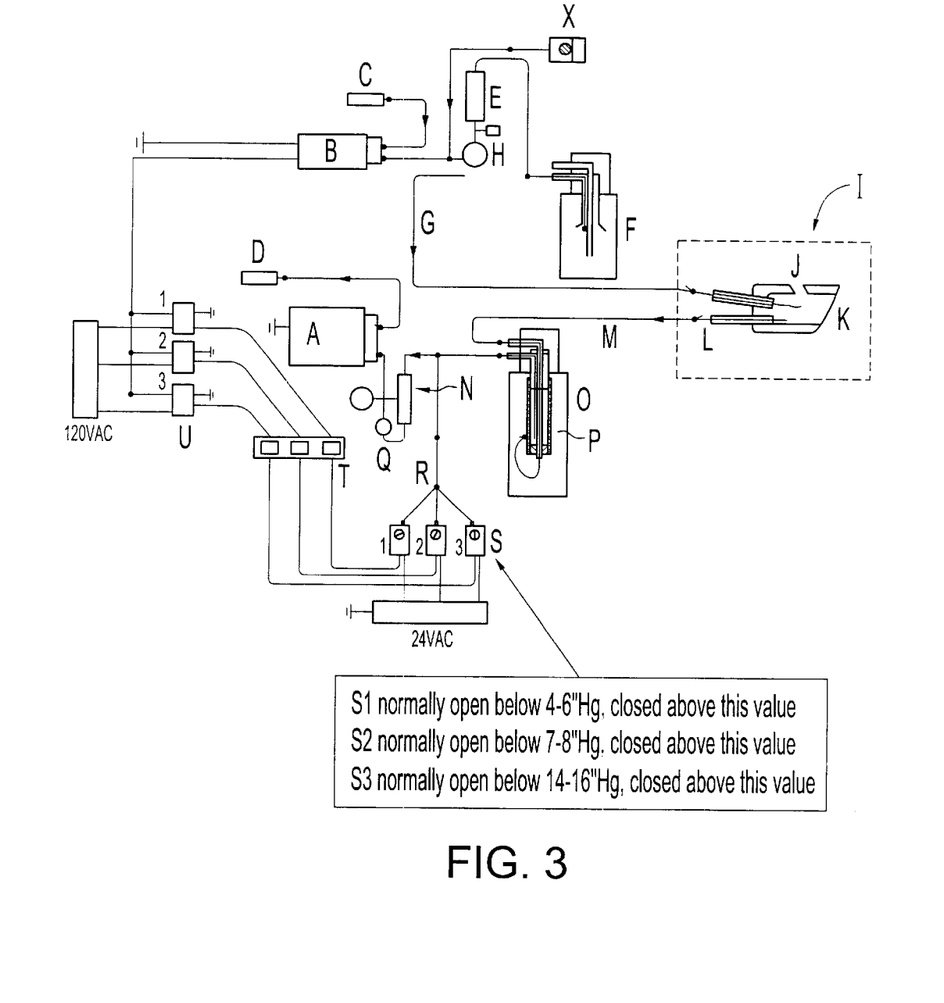
FIG. 3 shows a schematic of another embodiment of an MDA system.

A more complete MDA system is shown schematically in FIGS. 2 and 3. Included in the system are:

A. Vacuum pump, (rotary with CFM>1.5)
B. Compressor, (rotary with CFM>1.0)
C. 0.2 micron air filter, cleans air in compressor
D. Vacuum pump filter (25 micron, removes carbon dust from rotary vacuum pump) and muffler
E. Air flow or crystal flow gauge and pressure regulator or needle valve/relief valve assembly
F. Crystal dispenser
G. Tubing carrying air/crystal mixture to hand piece
H. Pressure regulator 0–15 psig
I. Hand piece assembly, injection molded, machined or liquid molded epoxy, polycarbonate, titanium or SS including a stainless steel tubing with quartz, ceramic or glass lining preferred orifice ~0.7 mm
J. Control line, orifice ~3 mm which controls vacuum when hand piece is in skin contact
K. Window, the primary orifice in skin contact
L. Vacuum line, including a stainless steel, rigid plastic or glass tubing attached thereto to remove spent crystals and debris
M. Tubing for handpiece to primary filter
N. Entrance to removable crystal receiver head
O. Outer rigid disposable container, plastic with sufficient strength to not collapse under 25 inches Hg vacuum
P. 5–65 micron macroporous polymer filter
Q. Vacuum gauge 0–30 inches Hg, flow gauge 1 pm, and vacuum leak valve assembly
R. Manifold to two or more electromechanical vacuum sensors which have been pre-set to different values
S. Pressure/vacuum sensors
T. Switches
U. Relays, for activation/deactivation of the compressor
V. Manual/computer control selection switch and logic board
W. 3-way main solenoid control valve
X. By-pass valve, closes when compressor on
Y. Vacuum sensor on microprocessor board
Z. Microprocessor board and e-prom Note, in MDA systems where the compressor does not run continuously, the solenoid valve W may be omitted (see FIG. 3). Also, the system shown in FIG. 2 contains both manual control mechanisms (sensor S1, S2 and S3 in conjunction with switches T and relays U) and one embodiment of an microprocessor controlled pressure switch means (sensor Y and microprocessor). Both control mechanisms are not required, for instance, as shown FIG. 1, only the manual control mechanism is shown.

The Handpiece

Figure 4A:
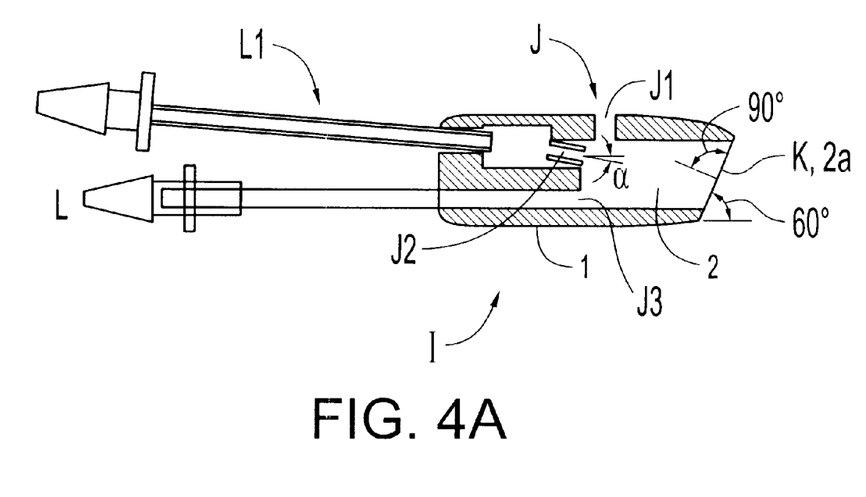
FIGS. 4A and 4B show cross sections of one embodiment of the handpiece.

The handpiece cross section is shown in FIG. 4a. Shown is a body 1, having an interior cavity 2 which opens forming a window K. Body 1 is adapted to be easily held in the hand much like a pencil. Positioned on the body are a compressor line L1, a vacuum line L and a control line J. The compressor line LI, vacuum line L and control line J are in fluid communication with the cavity 2. By "lines" is meant the opening in the body 1 into the cavity 2. Tubes maybe be inserted into the lines as is shown in FIG. 4a. Control line J has one end J1 which is open or can be opened to the exterior of the body 1. As shown, control line J is on the top center of the body 1. This placement of the control line J allows the operator, when holding the handpiece I, to place a fingertip over the open end J1 of the control line J, thereby closing the open end J1. Obviously, the control line J could be placed in the system so that the control line is in fluid contact with the cavity 2 while having a tubing or other conduit connected to the control line J to "remote" the control line from its placement in the system to the operator. It is preferred that the control line J be positioned on the headpiece as shown, so that the change in cavity pressure due to operator action of closing/opening the control line is not subject to delays. As will be discussed later discussed, the control line J, in conjunction with a pressure sensitive device, will be used to control activation of the compressor B. The control line J should be sized in comparison to the crystal injection orifice J2 size and vacuum nozzle orifice J3 size to allow a 10–25% drop in the vacuum when the operator's finger is raised. For instance, in the unit shown in FIG. 4a, with a 0.7 mm exit orifice, a control line of diameter 3 mm has been used when the compressor is creating pressures in the range of 0.10–10 psig measured at the handpiece. As later described, this pressure change is sensed by an appropriate device to activate/deactivate the compressor. The handpiece I may have an additional line or port to accommodate a pressure sensor (see FIG. 1).

A porous plastic or glass insert can be placed in the control line to isolate the abrasive flow from the finger of the operator and prevent microbial entry into the hand. The handpiece I can be composed of polycarbonate, epoxy, stainless steel or titanium. The nozzle or orifices can be composed of ceramic, glass, stainless steel or titanium. The entry and exit tubes and/or orifices, which connect the abrasive dispenser and compressor respectively, can be composed of stainless steel, titanium, plastic, ceramic or glass.

It is preferred that the compressor line L1 have an insert to protect the body 1 from being degraded by the flowing abrasive particles through this line or port. Suitable materials for the insert are a titanium, ceramic or glass insert lining. The inserts can be sized to adjust the exit orifice of the compressor line; for instance, for abrasive particles in the 50–200 mesh range, an exit orifice of 0.5 to 1.5 mm is preferred. Alternatively, the insert could be a sleeve with a tip placed thereon for setting the orifice size. The vacuum line L may also have an insert, such as a glass insert. As shown in FIG. 4a, the compressor line and vacuum line both have inserts, with an expansive plug end distal from the body 1 for holding flexible tubing.

As shown, the opening K or window 2a of the cavity 2 forms an angle of about 60 degrees. The angle is present so that when the window 2a is placed against the skin, the operator's hand, holding the handpiece, is at a comfortable angle, much like holding a pencil. For instance, while the window 2a angle could be 90 degrees, the operator would have to hold the handpiece perpendicular to the skin surface, which can be uncomfortable for a lengthy procedure and result in less operator control of the placement of the window 2a.

Also as shown, the compressor line L1 enters the body at an angle alpha. In the embodiment shown, compression line angle alpha in conjunction with the angle of the window face 2a and angle of exit orifice J2 results in a particle flow normal or perpendicular to the window face 2a. This configuration allows the energy of the flowing abrasive particles to be fully used for abrasion. Other angular configurations can be used if a tangential component of particle velocity is needed, for instance, to remove fine wrinkles.

Figure 7:
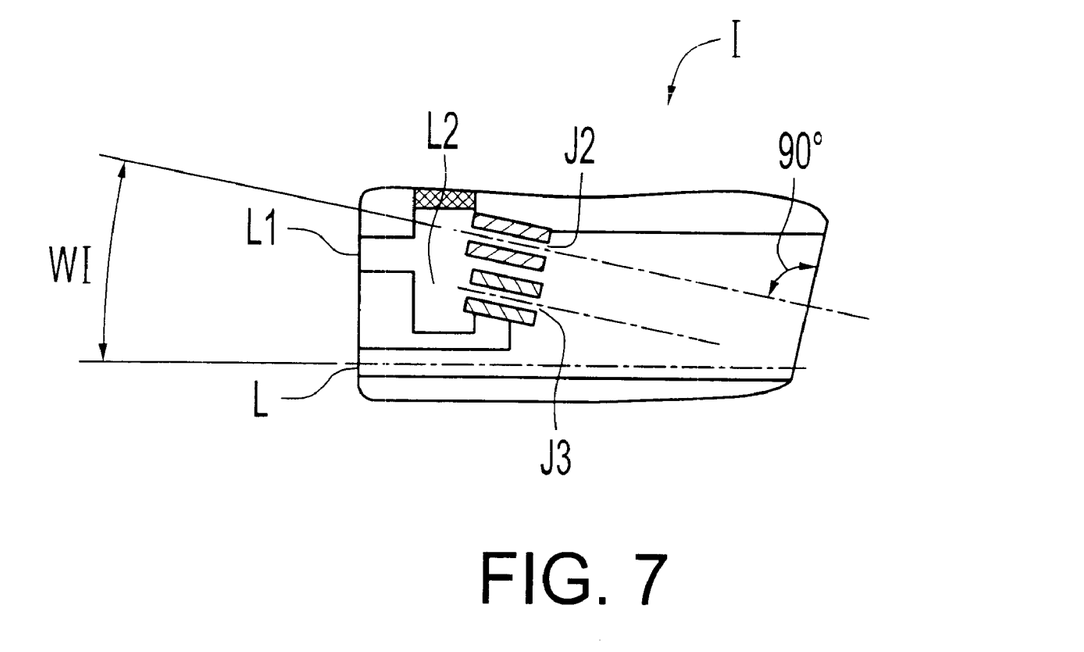
FIG. 7 shows a cross section through another embodiment of the handpiece.

The handpiece I shown in FIG. 7 is designed for treating large areas. As shown, the compressor line L1 includes a feed chamber L2 and two exit orifices J2 and J3. By multiplying the number of exit orifices, the treating area can be enlarged without changing the size of the exit orifices. For treating large surface areas, the handpiece in FIG. 7 is preferred. The device shown in FIG. 7 has a larger width WI than the device shown in FIGS. 4a and 4b to accommodate the additional exit orifices. However, the depth DP of the device in FIG. 7 is comparable to that in FIG. 4b. It is desired that the depth of the handpiece be suited for ease of grasping, which provides the operator better control of handpiece during treatment.

Figure 4B:
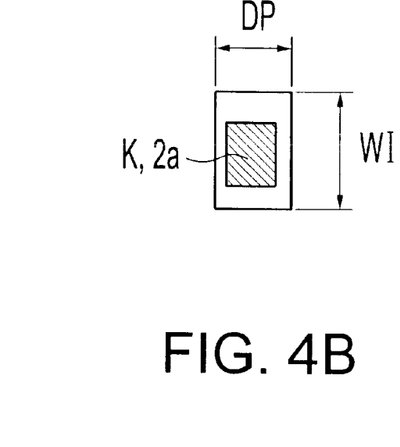

The exit window 2a of the device shown in FIG. 4b, in cross section, is shown as rectangular, although the cross section can be oval shaped or other shape. It is preferred that the exit window be oval or rectangular shaped over a circular or square window, as it allows for better overlap of adjacent strokes of the handpiece during treatment. Furthermore, if a circular exit window were used, the depth DP of the device in FIG. 7 would have to be enlarged, making it more difficult to grasp.

Pressure Switch Means

Activation/deactivation of the compressor B is accomplished by sensing pressure changes in the system during operation. In operation of the system, the handpiece window 2a is placed against the skin area to be treated causing an increase in vacuum level (i.e. a decrease in pressure) in the cavity 2 area due to the occlusion of the window 2a by the skin. The control line J is now used as a pressure regulator: when the line is closed, the vacuum level in the cavity increases; when the control line is open, the vacuum level decreases, as the cavity is open to the atmosphere through the control line. Consequently, the pressure present in the cavity 2a (or any area in fluid communication with the cavity) is an indicator that the device is "in use" (placed against the skin with control port closed) or "not in use" (either not against the skin, or against the skin with the control port open). To control the activation/deactivation of the compressor B, a pressure switch means is placed in the system. The pressure switch means detects the pressure levels (or the change of the pressure levels in the system, such as a difference or a differential (slope)) in the system, and activates/deactivates the compressor accordingly. Activation/deactivation should be interpreted broadly to include switching the compressor on/off, or in systems where the compressor runs continuously, shunting the air flow (such as through a solenoid valve W shown in FIG. 2) into the mixing bottle F (activation) or away from the mixing bottle F, such as to the atmosphere (deactivation). For instance, the pressure switch means may include a series of pressure switches (shown as the combination of pressure sensors S, switches T and relays U). Switches can be microprocessor controlled switches, microswitches, solenoid activated switches, contact switches, or any other type of switch device). Shown in FIG. 2 are three pressure settings, S1, S2 and S3, in conjunction with switches and relays for the pressure switch means, all being located between the collecting bottle and the vacuum pump. Obviously, the pressure switch means could be fluidly connected to other portions of the system.

Each switch is designed to operate at a particular pressure setting. Typical settings are 4–6 inches of mercury below atm. (S1), 7–8 inches of mercury below atm (S2), and 14–16 inches of mercury below atm. In use, the operator must select the appropriate pressure setting based upon the type of procedure to be undertaken.

The operator will place the handpiece window 2a against the skin. With the control line J open, the vacuum level present in the cavity 2 should be less than that needed to activate the chosen pressure setting for the pressure switch means. However, when the control line J is closed or occluded, the pressure in the cavity falls (increased vacuum) and should be sufficient to operate the chosen pressure switch means, thereby activating the compressor. When the closed control line J is later opened, the pressure in the cavity rises back above that needed to operate the pressure switch means, so the switch means changes state, deactivating the compressor. Consequently, the operator, by closing/opening the control line J activates/deactivates the compressor. The pressure may be independently adjusted through the pressure regulator or needle valve "leak".

If the device needs calibration, the operator places the hand piece on a plastic or other nonporous strip or pad. The operator closing the control line, and the vacuum level is then altered via the turning of a regulator or needle valve "leak" until the vacuum level is reached which activates the selected switch, thereby activating the compressor. When the operator removes a finger from the control line the vacuum is reduced and the compressor is turned off. The pressure activated electromechanical switches currently used have a sensitivity of about 0.5 inches of Hg.

Figure 8:
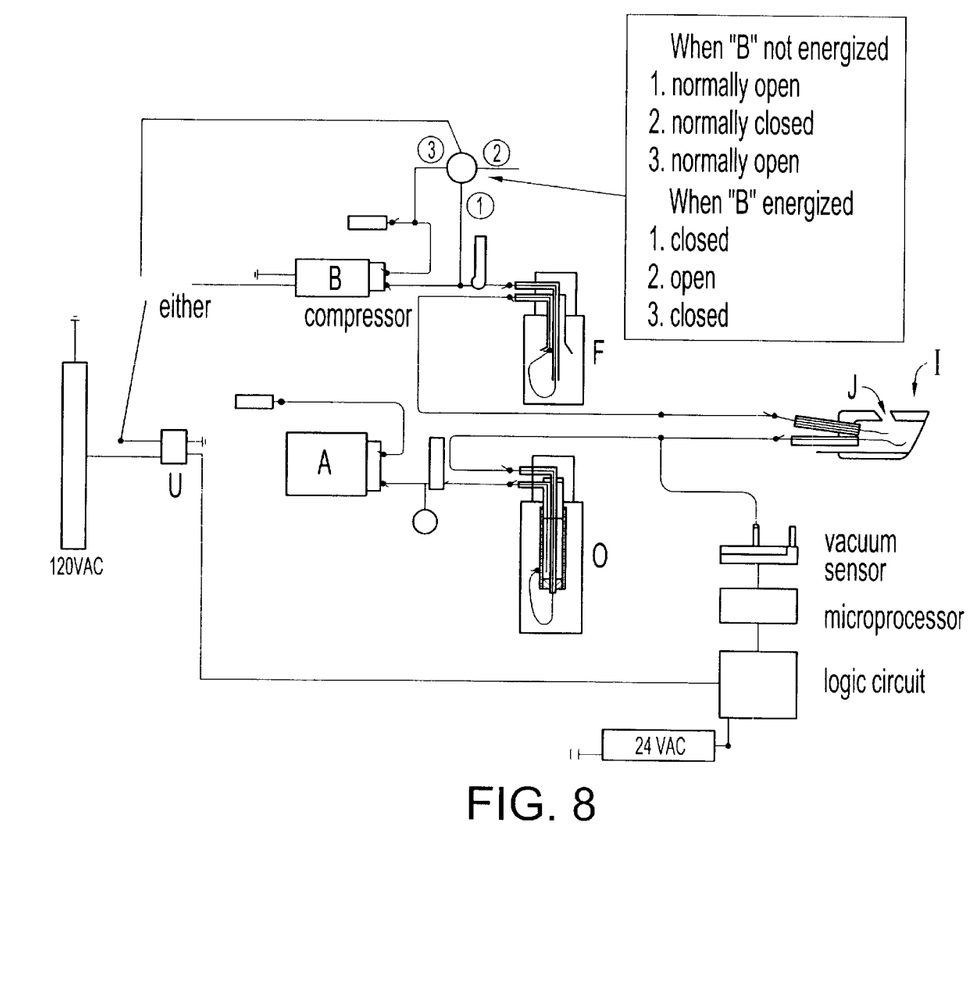
FIG. 8 shows a schematic of a basic MDA system showing placement of the pressure switch means in the vacuum line.

Other pressure switch means may be used. For instance, a pressure-sensing probe may be placed in the system and combined with a logic circuit or microprocessor for activation/deactivation of the compressor. For instance, a pressure sensor may be placed in the handpiece cavity (shown in FIG. 1 as 13) or placed in a position in fluid communication with the cavity, such as between the handpiece and the compressor pump (FIG. 8). The logic circuit can be configured to activate based upon the pressure exceeding a threshold level, much like the prior described switches, or alternatively, the logic circuit may compare recent pressure readings against prior pressure readings to monitor the rate of change of the pressure in the cavity ("differential sensing"). If the rate of change of the pressure exceeds a threshold value (one value used is −0.25 inches of mercury/per 0.25 seconds) the compressor would activate. Similarly, a second threshold (such as +0.25 inches of mercury/per 0.25 seconds) would be used by the logic circuit to deactivate the compressor. The differential sensing type of control system allows the operator to choose any vacuum setting independent of the pressure (i.e., as long as the pressure setting does not result in a CFM which exceeds the ability of the vacuum pump to extract). Alternatively, the pressure sensor probe may be placed in the lines leading to/or away from the handpiece, or any other position in the system, which is in fluid communication with the cavity in the handpiece.

Figure 9:
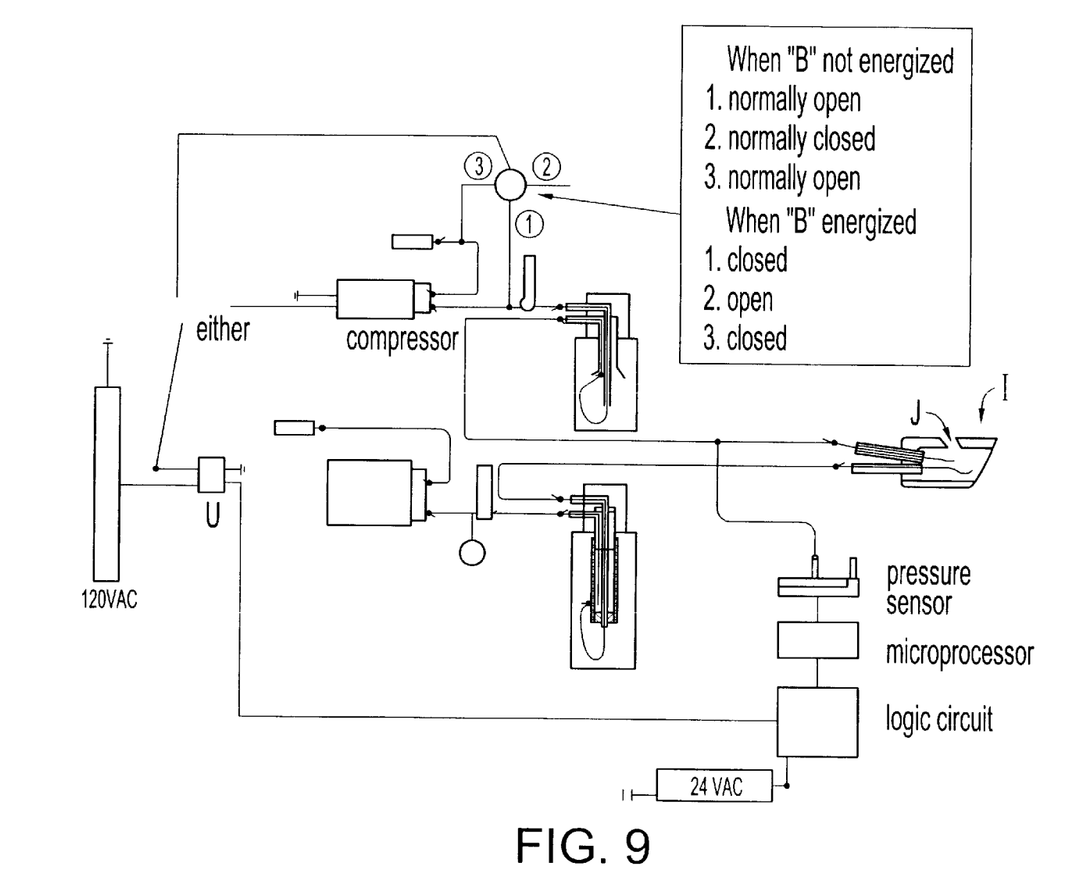
FIG. 9 shows a schematic of a basic MDA system showing placement of the pressure switch means in the compressor line.

For instance, the pressure sensing probe may also be placed in the input line, as shown in FIG. 9, or be in fluid communication with the input line. In this case, the system may be configured to detect a pressure "spike" for compressor activation. The nozzle restriction (orifice) within the handpiece I results in a flow resistance, which in turn results in a pressure rise within the tubing before the orifice. This is the case whether the vacuum pump is "pulling" the air/crystal through the hand piece or the compressor is "pushing". When the handpiece I is in contact with the skin and the control line J is closed, a pressure spike in tubing leading to L1 will be seen by the pressure sensor. The microprocessor/logic circuit interprets this as an "activate" command for the compressor. Action of the compressor increases the pressure within the tubing going to the handpiece, which will generally equilibrate after the unit is operated (the operator moves the handpiece across the skin. When the control line J is opened, the microprocessor/logic circuit interprets the rapid decrease in pressure in tubing leading to Li as a command to "deactivate" the compressor.

Figure 10:
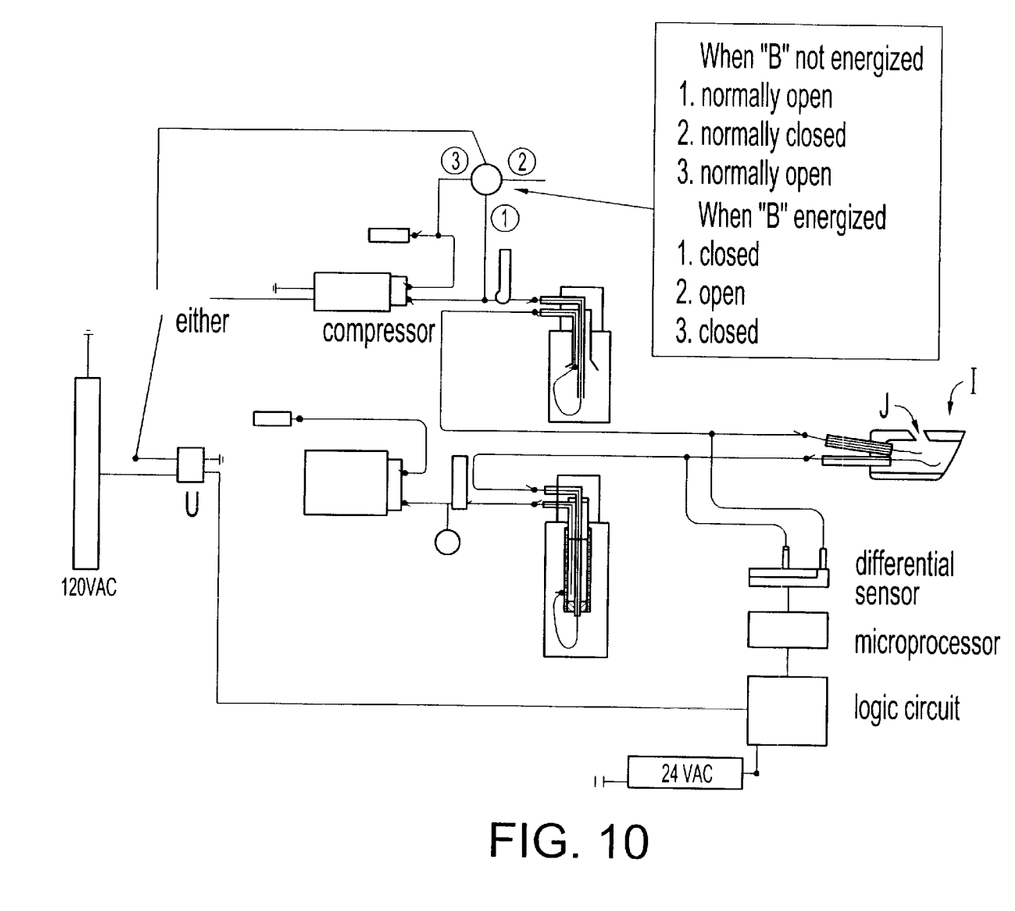
FIG. 10 shows a schematic of a basic MDA system showing placement of the pressure switch across the vacuum and compressor lines.

Another type of pressure sensing device is one connected to both lines L and L1 to measure pressure differences across the inflow and outflow lines. In one configuration, shown in FIG. 10, the compressor B is activated when a positive pressure differential is observed in the measured pressure difference (i.e. the differential of the differences) between L1 and L. Flow is maintained until a pre-determined pressure differential drop is noted at which time the compressor B is deactivated, and an optional purge valve triggered to eliminate air pressure surge. The vacuum pump A may be optionally either turned off or left on for debris removal.

When the pressure sensor is placed in the cavity or directly in the compressor or vacuum line with the possibility of crystal contact with the sensor, a 5–25 micron macroporous polymer filter can be used to isolate the sensor. This can be incorporated into the hand piece as a third tube with a disposable filter element.

In all of the embodiments, a pressure sensor is used in conjunction with a switch (a pressure solenoid may combine the features of both sensor and switch) where the switch is responsive to the pressure sensor. "responsive" is used in the sense of both directly responsive (such as in the manual operations mode, where the pressure sensor directly indicates to a switch to change state) and indirectly responsive, where the pressure sensor may output readings to a microprocessor, and the microprocessor or logic circuit, based upon the pressure sensors readings or a manipulation of those readings, determines to change the state of the switch to activate/deactivate the compressor (obviously, the switch could be incorporated into the microprocessor or logic circuit).

Although the present invention has been described in terms of specific embodiments, it is anticipated that alterations and modifications thereof will no doubt become apparent to those skilled in the art which are intended to be included within the scope of the following claims.

I claim:

1. In an MDA system having an air source and a vacuum generating device, a handpiece comprising:
   a body adapted to be hand held by an operator, said body having an exterior surface and an interior cavity, said interior cavity opening to said exterior surface of said body, said handpiece further having a compressor line positioned on said body connectable to said air source, a vacuum line positioned on said body connectable to said vacuum generating device, and a control line positioned on said body, said compressor line, said vacuum line and said control line being in fluid communication with said interior cavity, said control line having at least one open end.

2. A handpiece according to claim 1 wherein said body has a top portion and said control line is positioned on said top portion to be occludable by action of the operator's fingers.

3. A handpiece according to claim 1 wherein said compressor line includes an exit orifice positioned in or near said cavity.

4. An MDA system having an air source, a vacuum generating device and a handpiece, a first path fluidly connecting said air source with said handpiece, second path fluidly connecting said handpiece with said vacuum generating device, said MDA system further having a pressure sensor and a switch, said switch operatively connected to said air source for activating/deactivating said air source, said switch responsive to said pressure sensor.

5. An MDA system according to claim 4 where said pressure sensor is positioned to sense pressure in said first path.

6. An MDA system according to claim 4 wherein said pressure sensor is positioned to sense pressure in said second path.

7. An MDA system according to claim 4 wherein said pressure sensor is positioned to sense pressure in said handpiece.

8. An MDA system according to claim 4 wherein said pressure sensor is positioned to sense pressure in said first and said second path.

9. An MDA system according to claim 4 further having a microprocessor, said microprocessor receiving and processing signals from said pressure sensor, said switch being responsive to said processed signals.

10. An MDA system according to claim 9 wherein said processing of said signals includes calculating differentials of said received pressure sensor signals.

11. An MDA system having an air source, a vacuum generating device and a handpiece, a first path fluidly connecting said source of air with said handpiece, a second path fluidly connecting said vacuum generating device with said handpiece, said MDA system further having a pressure switch means for activating/deactivating said air source.

12. An MDA system according to claim 9 wherein said pressure switch means includes a pressure sensor positioned to sense pressure in said first path.

13. An MDA system according to claim 11 wherein said pressure switch means includes a pressure sensor positioned to sense pressure in said second path.

14. An MDA system according to claim 11 wherein said pressure switch means includes a pressure sensor positioned to sense pressure in said handpiece.

15. An MDA system according to claim 11 wherein said pressure switch means includes a pressure sensor is positioned to sense pressure in said first and said second path.

16. A handpiece for use in an MDA system comprising:
   a body adapted to be hand held, said body having an exterior surface and an interior cavity, said interior cavity opening to form a window to said exterior surface of the body, said handpiece further having a compressor line positioned on said body connectable to a source of compressed air, a vacuum line positioned on said body connectable to a vacuum source, and a control line positioned on said body, said compressor line, said vacuum line and said control line being in fluid communication with said interior cavity, said control line having one open end.

17. A handpiece according to claim 16 wherein said window forms a plane, and said compressor line further has an orifice positioned therein so that particles ejected from said orifice intersects said plane of said window at an angle of about 90 degrees.

18. A handpiece according to claim 16 wherein said window is oval or rectangular shaped.

* * * * *